United States Patent [19]
Siegler

[11] Patent Number: 5,941,394
[45] Date of Patent: Aug. 24, 1999

[54] MEDICINE ORGANIZER

[76] Inventor: Kathleen R. Siegler, 212 Elmwood, Clawson, Mich. 48017

[21] Appl. No.: 09/130,009

[22] Filed: Aug. 6, 1998

Related U.S. Application Data

[60] Provisional application No. 60/055,394, Aug. 6, 1997.

[51] Int. Cl.⁶ .................................................. B65D 69/00
[52] U.S. Cl. .......................... 206/571; 206/366; 206/534; 206/459.5
[58] Field of Search ..................................... 206/363, 364, 206/365, 366, 459.5, 562, 564, 534, 570, 571; 220/506

[56] References Cited

U.S. PATENT DOCUMENTS

| | | |
|---|---|---|
| D. 301,615 | 6/1989 | Vitart-Liva . |
| D. 359,127 | 6/1995 | Biesecker . |
| 2,435,994 | 2/1948 | Zukerman ............................. 206/366 |
| 4,155,446 | 5/1979 | Aronson .............................. 206/459.5 |
| 4,250,998 | 2/1981 | Taylor ................................... 206/571 |
| 4,349,338 | 9/1982 | Heppler ............................... 206/459.5 |
| 4,850,484 | 7/1989 | Denman ................................ 206/366 |
| 4,863,451 | 9/1989 | Marder ................................. 206/366 |
| 5,190,169 | 3/1993 | Sincock ................................ 206/206 |
| 5,303,822 | 4/1994 | Wengyn et al. ...................... 206/366 |
| 5,823,363 | 10/1998 | Cassel ................................. 206/366 |
| 5,850,917 | 12/1998 | Denton et al. ....................... 206/366 |

*Primary Examiner*—David T. Fidei
*Attorney, Agent, or Firm*—Gifford, Krass, Groh, Sprinkle, Anderson, & Citkowski, P.C.

[57] ABSTRACT

An organizer for medicine of the type which should be periodically dispensed by syringe, such as insulin, is disclosed. The organizer includes a housing having at least two wells wherein each well is dimensioned to hold a vial of the medicine. A plurality of circumferentially spaced openings are provided around each well and each opening is dimensioned to receive and support one syringe. Indicia, such as a braille and/or color strip, is provided on the housing adjacent each well which represents the time of day that the medicine in this vial should be taken.

10 Claims, 2 Drawing Sheets

MEDICINE ORGANIZER

RELATED APPLICATION

This application claims the benefit of United States Provisional Application Ser. No. 60/055,394 filed Aug. 6, 1997.

BACKGROUND OF THE INVENTION

I. Field of the Invention

The present invention relates generally to an organizer for medicine and, more particularly, to an organizer for medicine of the type which should be dispensed periodically by syringe at certain times throughout the day.

II. Description of the Prior Art

Certain types of medicine, such as insulin, must be periodically dispensed by syringe throughout the day. The failure to take the proper dose of the medicine at the appropriate time can result in a life-threatening situation.

Unfortunately, many persons which require such medicine are either aged and/or visually impaired. This is particularly true for diabetes which frequently causes partial or even total blindness in the patient.

Previously, there have been no medicine organizers for medicines of the type which must be periodically dispensed by syringe throughout the day to ensure that the patient receives the proper dose of medicine and at the proper time.

SUMMARY OF THE PRESENT INVENTION

The present invention provides an organizer for medicine which overcomes all of the above-mentioned disadvantages of the previously known devices.

In brief, the organizer of the present invention comprises a housing having at least two wells wherein each well is dimensioned to hold a multi-dose vial of the medicine. A plurality of circumferentially spaced openings are then provided around each well and each opening is dimensioned to receive and support one syringe. There are preferably seven openings around each well wherein one opening corresponds to each day of the week.

Preferably, a cap is provided to cover each well with its associated openings. The cap may be either threadably secured to the housing or a push on cap.

Indicia means, such as a braille and/or color strip, is provided on the housing adjacent each well representing the time of day in which the medicine should be taken. For example, the color yellow could represent morning, the color red representing afternoon and the color black representing evening could be used as the color strips on the housing. Similar indicia are also provided on the caps which are associated with each of the wells.

In lieu of the color strip, the entire housing surrounding the well may be color coded.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
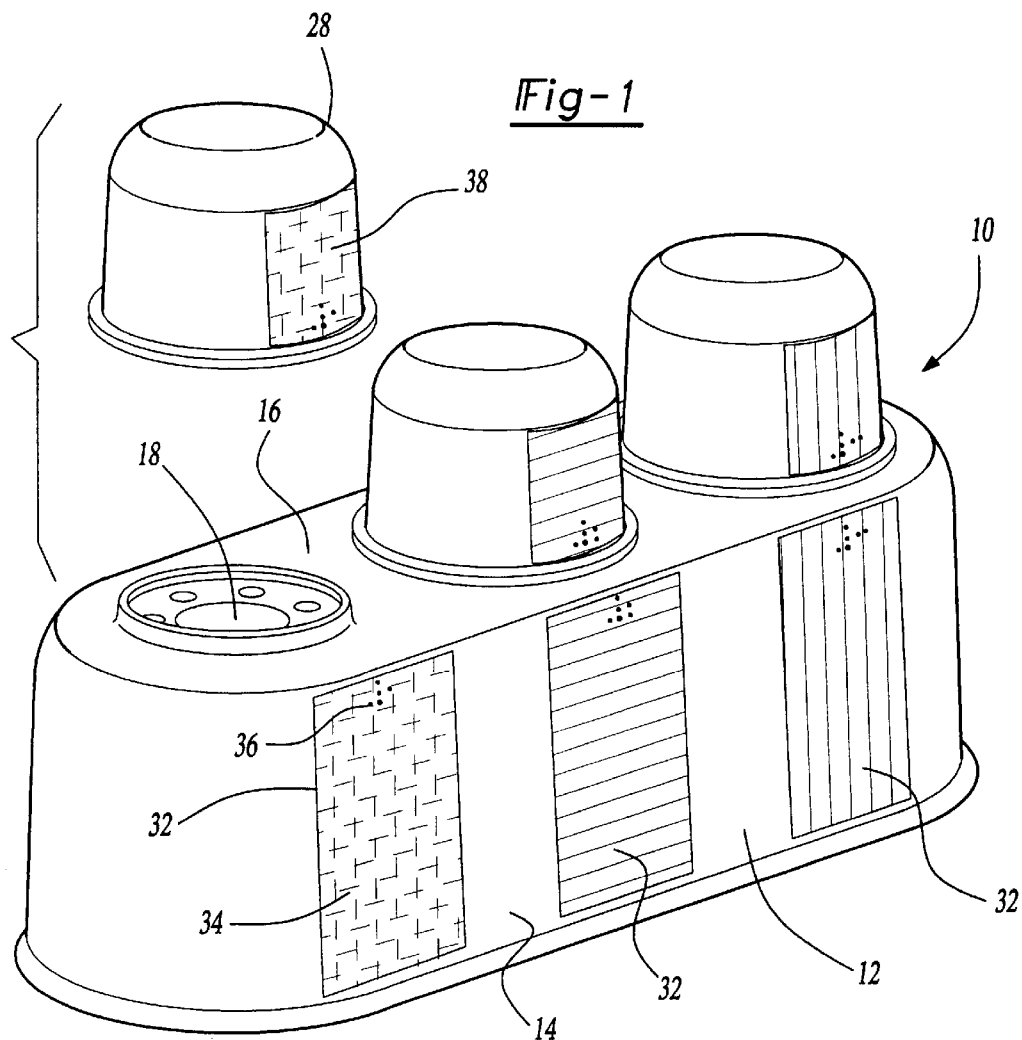
FIG. 1 is an elevational exploded view illustrating a preferred embodiment of the present invention.
Figure 2:
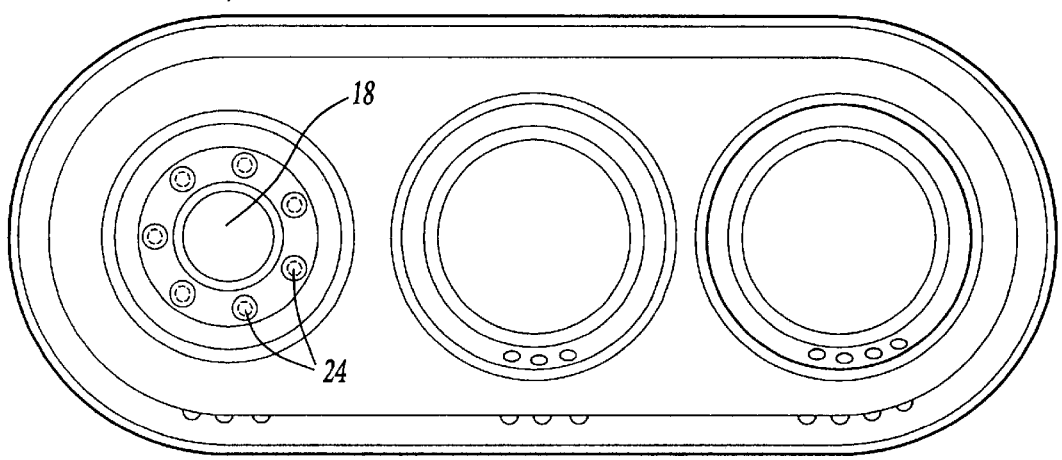
FIG. 2 is a top view of the preferred embodiment of the present invention and with one cap removed.

With reference first to FIGS. 1 and 2 of the patent drawing, a preferred embodiment of the organizer 10 of the present invention is thereshown and comprises a housing 12 which is preferably constructed of a plastic material. The housing 12 includes a front 14 as well as a top 16.

At least two and preferably three wells 18 (only one illustrated in FIGS. 1 and 2) are provided in the top 16 of a housing 12 such that the wells 18 are linearly aligned with each other. Furthermore, each well 18 is dimensioned to receive a medicine vial 20 (FIG. 3) of the medicine which should be periodically dispensed throughout the day.

Figure 3:
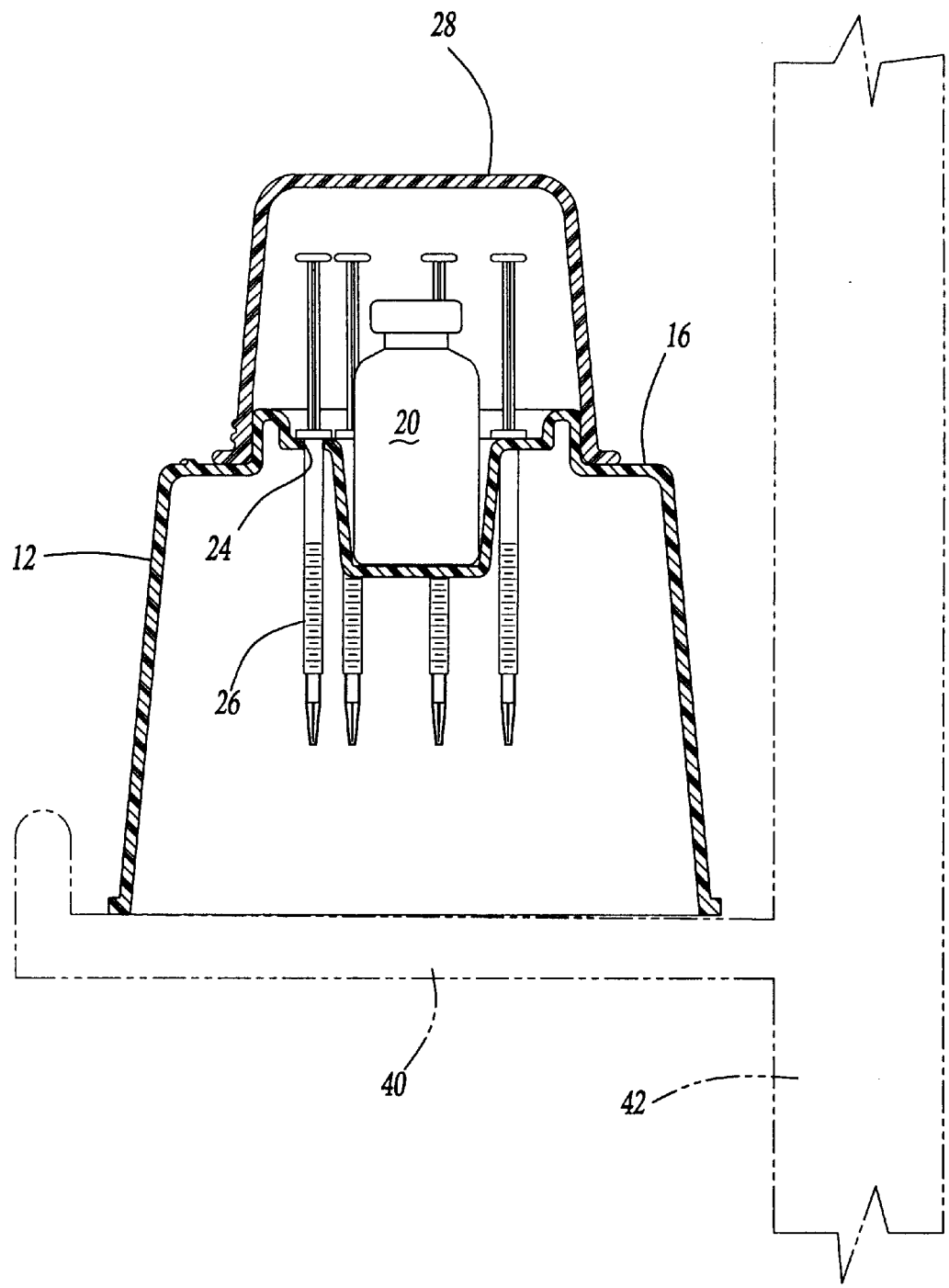
FIG. 3 is a sectional view taken substantially along line 3—3 in FIG. 2 and enlarged for clarity.

As best shown in FIGS. 2 and 3, a plurality of openings 24 are circumferentially spaced around each well 18. As best shown in FIG. 3, each opening 24 is dimensioned to receive and support one syringe 26. Since there are preferably seven openings 24 around each well 18, the organizer 10 of the present invention is designed to hold a one-week supply of medicine with each opening 24 representing one day of the week.

With reference now to FIGS. 1 and 3, a cap 28 is associated with each well 18. The cap 28 is dimensioned to overlie and cover not only its associated well 18 but also the openings 24 surrounding the associated well 18. The cap 28 may be either a push-on cap, as illustrated in FIG. 3, or a threaded cap.

With reference now especially to FIG. 1, indicia means 32 are provided on the front 14 of the housing 12 adjacent each well 18. The indicia means 32 is indicative of the time of day that the medicine within its associated well 18 should be taken. In the preferred embodiment of the invention, the indicia means 32 comprises both a color strip 34 as well as braille 36 to accommodate sight-impaired patients. For example, the color yellow could correspond to morning, the color red could correspond to afternoon and the color black could correspond to evening.

Similar indicia means 38 are also provided on the cap 28 associated with each well 18.

In lieu of the color strip, the entire housing portion surrounding the well may be color coded.

With reference now especially to FIG. 3, the housing 12 is dimensioned so that the entire housing 12 with its contained medicine vials 20 can fit on a door shelf 40 of a conventional refrigerator door 42. Medicines such as insulin, of course, must be refrigerated.

From the foregoing, it can be seen that the present invention provides a unique organizer for medicine of the type which is periodically dispensed by a syringe. The organizer of the present invention is especially designed to accommodate a one-week supply of medicine with up to three doses per day. It will be understood, however, that additional doses of medicine per day could be easily accommodated by simply adding additional wells beyond the three wells shown in the drawing.

Having described my invention, however, many modifications thereto will become apparent to those skilled in the art to which it pertains without deviation from the spirit of the invention as defined by the scope of the appended claims.

I claim:

1. An organizer for medicine which should be periodically dispensed by a syringe comprising:

a housing having at least two wells, each well being dimensioned for holding a vial of medicine, a plurality of circumferentially spaced openings provided around each well, each opening dimensioned to receive and support one syringe, indicia means on said housing adjacent each well, said indicia means representing a time of day the medicine in the vial should be taken.

2. The invention as defined in claim 1 and including a cap associated with each well, said cap dimensioned to overlie and cover its associated well and the openings provided around said associated well.

3. The invention as defined in claim 2 and comprising second indicia means on said cap which correspond to said first mentioned indicia means on said housing.

4. The invention as defined in claim 1 wherein seven said openings are provided around each well.

5. The invention as defined in claim 1 wherein said housing includes at least three wells.

6. The invention as defined in claim 5 wherein said wells are linearly aligned with each other.

7. The invention as defined in claim 6 wherein said housing is dimensioned to fit in a door tray of a conventional refrigerator.

8. The invention as defined in claim 1 wherein said indicia means comprises a color strip.

9. The invention as defined in claim 1 wherein said indicia means comprises braille.

10. The invention as defined in claim 1 wherein said indicia means comprises coloring substantially the entire housing surrounding its associated well.

\* \* \* \* \*